United States Patent
Haase et al.

(10) Patent No.: US 12,198,335 B2
(45) Date of Patent: Jan. 14, 2025

(54) AUTOMATED CORONARY ANGIOGRAPHY ANALYSIS

(71) Applicant: KONINKLIJKE PHILIPS N.V., Eindhoven (NL)

(72) Inventors: Christian Haase, Hamburg (DE); Dirk Schaefer, Hamburg (DE); Michael Grass, Buchholz in der Nordheide (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 409 days.

(21) Appl. No.: 17/618,445

(22) PCT Filed: Jun. 29, 2020

(86) PCT No.: PCT/EP2020/068273
§ 371 (c)(1),
(2) Date: Dec. 11, 2021

(87) PCT Pub. No.: WO2020/260701
PCT Pub. Date: Dec. 30, 2020

(65) Prior Publication Data
US 2022/0351369 A1    Nov. 3, 2022

(30) Foreign Application Priority Data

Jun. 28, 2019  (EP) .................................. 19183278

(51) Int. Cl.
*G06T 7/00* (2017.01)
*A61B 6/00* (2006.01)
*A61B 6/50* (2024.01)

(52) U.S. Cl.
CPC ............ *G06T 7/0012* (2013.01); *A61B 6/481* (2013.01); *A61B 6/504* (2013.01);
(Continued)

(58) Field of Classification Search
CPC ............... G06T 7/0012; G06T 2200/24; G06T 2207/10116; G06T 2207/20081;
(Continued)

(56) References Cited

U.S. PATENT DOCUMENTS

2006/0079778 A1  4/2006  Mo
2014/0121513 A1  5/2014  Tolkowsky
(Continued)

FOREIGN PATENT DOCUMENTS

CN    108280827 A    7/2018
JP    2013236960 A   11/2013
(Continued)

OTHER PUBLICATIONS

International Search Report and Written Opinion of PCT/EP2020/068273, dated Oct. 8, 2020.
(Continued)

*Primary Examiner* — Bobbak Safaipour (57) ABSTRACT

A method and apparatus for analyzing diagnostic image data are provided in which a plurality of acquisition images of a vessel of interest having been acquired with a pre-defined acquisition method is received at a trained classifying device and classified, by the classifying device, to extract at least one quantitative feature of the vessel of interest from at least one acquisition image of the plurality of acquisition images. The at least one quantitative feature is then output associated with the at least one acquisition image while the acquisition of the diagnostic image data is still in progress and one or more adjustable image acquisition settings are adjusted based on the at least one quantitative feature to optimize the acquisition of the diagnostic image data.

20 Claims, 2 Drawing Sheets

(52) U.S. Cl.
CPC . *G06T 2200/24* (2013.01); *G06T 2207/10116* (2013.01); *G06T 2207/20081* (2013.01); *G06T 2207/30096* (2013.01); *G06T 2207/30101* (2013.01)

(58) Field of Classification Search
CPC . G06T 2207/30096; G06T 2207/30101; G06T 2207/10081; G06T 2207/10088; G06T 2207/10132; G06T 2207/20084; G06T 2207/20104; G06T 2207/30104; A61B 6/481; A61B 6/504; A61B 6/032; A61B 6/463; A61B 6/5294; A61B 6/541; A61B 6/5217; A61B 6/545; A61B 6/487; A61M 5/007; G06N 3/08; G06N 3/045; G06F 18/214; G06F 18/241
See application file for complete search history.

(56) References Cited

U.S. PATENT DOCUMENTS

| | | | |
|---|---|---|---|
| 2015/0206614 A1 | 7/2015 | Roh | |
| 2015/0332455 A1 | 11/2015 | Kobayashi | |
| 2016/0278725 A1* | 9/2016 | Van Nijnatten | A61B 6/461 |
| 2017/0262733 A1 | 9/2017 | Gulsun | |
| 2017/0311921 A1 | 11/2017 | Feuerlein | |
| 2018/0042566 A1 | 2/2018 | Roffe | |
| 2019/0076105 A1* | 3/2019 | Haase | A61B 6/507 |
| 2020/0175677 A1* | 6/2020 | Mavroeidis | G06T 7/0012 |
| 2021/0038090 A1* | 2/2021 | Kang | G06T 7/62 |
| 2021/0174500 A1* | 6/2021 | Van Pelt | G16H 50/50 |
| 2021/0248762 A1* | 8/2021 | Pfister | G06T 7/149 |
| 2022/0022759 A1* | 1/2022 | Gong | A61B 5/7257 |
| 2022/0175332 A1* | 6/2022 | Haase | A61B 6/504 |
| 2024/0078676 A1* | 3/2024 | Van Pelt | G06T 11/60 |
| 2024/0081758 A1* | 3/2024 | Carelsen | A61B 18/1492 |
| 2024/0090876 A1* | 3/2024 | Nachtomy | A61B 8/12 |
| 2024/0290224 A1* | 8/2024 | Wortmann | G09B 23/285 |

FOREIGN PATENT DOCUMENTS

| | | |
|---|---|---|
| JP | 2015136622 A | 7/2015 |
| JP | 2015217170 A | 12/2015 |
| WO | 2016087396 A1 | 6/2016 |
| WO | 2019101630 A1 | 5/2019 |
| WO | 2020053099 A1 | 3/2020 |

OTHER PUBLICATIONS

Yasar, Ayse S. et al, "Comparison of a Safety Strategy Using Transradial Access and Dual-Axis Rotational Coronary Angiography with Transfemoral Access and Standard Coronary Angiography", Journal of Interventional Cardiology, 2013; vol. 26.

* cited by examiner

AUTOMATED CORONARY ANGIOGRAPHY ANALYSIS

CROSS-REFERENCE TO PRIOR APPLICATIONS

This application is the U.S. National Phase application under 35 U.S.C. § 371 of International Application No. PCT/EP2020/068273, filed on Jun. 29, 2020, which claims the benefit of European Patent Application No. 19183278.1, filed on Jun. 28, 2019. These applications are hereby incorporated by reference herein.

FIELD OF THE INVENTION

The present invention relates to a method for analyzing diagnostic image data, in particular X-ray angiographic image data, a corresponding apparatus and a respective computer program. In particular, the present invention relates to an improved method and apparatus that allow to automatically derive quantitative feature information from diagnostic image data that has been acquired using pre-defined acquisition settings and to use the thus derived quantitative feature information to adjust the pre-defined acquisition settings accordingly, thereby improving the quality of the acquisition process.

BACKGROUND OF THE INVENTION

Today, coronary disease is a widely-spread ailment in many societies. Various coronary diseases are known. In order to develop an appropriate treatment plan for each respective coronary disease, it is of great importance that the disease is correctly assessed, i.e. that the medical data from which the coronary disease may be evaluated is of high quality and high reliability.

One well-established method used in clinical practice for the assessment of coronary diseases is coronary X-ray angiography. Coronary angiography is typically performed by injecting a contrast agent into the blood vessels and subsequently irradiating the contrast agent-filled coronary vessels with X-ray radiation to acquire a sequence of angiographic images in which these vessels and, hence, the coronary vasculature are clearly visible. Hereby, the number and orientation of these angiographic image sequences, the contrast agent dose and the respective analysis of the image data may vary from one patient to another, making an objective analysis that is comparable for different patients very difficult.

In order to overcome these issues, improved acquisition approaches have been developed in which pre-defined acquisition settings are used to acquire the angiographic image sequences. Using these pre-defined acquisition settings reduces the variability in the acquired data since certain acquisition settings are known for each patient.

One such acquisition approach is the Xper Swing acquisition in which the angiographic image data is acquired at different orientations along a predefined repeatable trajectory with a pre-defined dose of contrast agent. An Xper Swing acquisition hereby provides the angiographic image data to be analyzed for evaluation of a particular coronary artery as a single image sequence. However, the quality of the angiographic image data acquired using Xper Swing still varies due to the optimization of certain acquisition settings being patient-dependent, due to the inter-patient variability of the anatomy, and due to the (remaining) variability in the acquisition settings.

As a result, automation of the data analysis is challenging. That is, automation of the analysis would require complex calculations that take account of all variabilities that may occur in the data for the different patients.

Thus far, an approach that allows for a reliable, repeatable, objective and efficient acquisition and analysis of diagnostic image data, such as angiographic image data, in particular diagnostic image data that has been acquired using certain predefined acquisition settings, has not been developed.

SUMMARY OF THE INVENTION

It is therefore an object of the present invention to provide a method and an apparatus that enable acquisition and analysis of diagnostic image data in a reliable, repeatable, objective and efficient manner.

More particularly, it is an object to provide a method and an apparatus for efficiently acquiring diagnostic image data using a medical imaging modality, such as X-ray angiography, with pre-determined acquisition settings in order to obtain reliable results that allow an objective and patient-independent assessment of the coronary disease. Even more particularly, it is an object of the invention to provide a method and an apparatus that allows to reduce the radiation dose and contrast agent dose that is delivered to a patient during image-based coronary disease assessment.

This object is achieved by a method for analyzing diagnostic image data comprising the steps of: receiving diagnostic image data comprising a plurality of acquisition images of a vessel of interest at a trained classifying device, the diagnostic image data having been acquired using a pre-defined acquisition method, classifying the diagnostic image data to extract at least one quantitative feature of the vessel of interest from at least one acquisition image of the plurality of acquisition images, outputting the at least one quantitative feature of the vessel of interest associated with the at least one acquisition image while the acquisition of the diagnostic image data is still in progress, and adjusting one or more adjustable image acquisition settings based on the at least one quantitative feature to optimize the acquisition of the diagnostic image data.

That is, the object is solved by a method which employs a trained classifying device, such as a convoluted neural network, to automatically analyze diagnostic image data already during acquisition of said diagnostic image data in order to adjust, during said ongoing acquisition, a set of adjustable acquisition settings, such as certain acquisition parameters, for optimizing the data acquisition for particular vessel properties, i.e. for particular patients.

The term diagnostic image data may hereby refer to a set of acquisition images representing a patient's vasculature. Hereby, the term vasculature may refer to a vessel tree or a single vessel. The term vasculature may particularly refer to one or more vessels of interest and/or segments thereof. The term vessel of interest may hereby refer to a vessel of the patient which shall be assessed—with respect to potential lesions and/or other diseases—using the diagnostic image data. In some embodiments, the acquisition images of the diagnostic image data may each represent a vessel of interest of the coronary vasculature.

The diagnostic image data may particularly comprise one or a plurality of acquisition images of said one or more vessels of interest. Hereby, the term acquisition image may typically be understood to refer to a single image acquired for the vessel of interest, whereby multiple acquisition images may be included in the diagnostic image data.

The plurality of acquisition images may particularly be acquired by a medical imaging modality, such as computed tomography (CT), ultrasound (US) imaging or magnetic resonance (MR) imaging. In some embodiments, the medical imaging modality may particularly correspond to X-ray angiography, even more particularly to X-ray angiography performed with a set of pre-defined acquisition settings, such as a pre-defined imaging trajectory and a pre-defined dose of contrast agent to be used.

In some embodiments, the medical imaging modality may be gated. Hereby, the gated medical imaging modalities may typically employ a gated reconstruction, in which the acquisition of the acquisition images is performed in parallel with acquisition of data providing information over the cardiac cycle, such as electrocardiogram (ECG) or photoplethysmographic (PPG) data. This data may hereby be used to gate the image acquisition and the reconstruction by means of respectively selected phase points of the cardiac cycle.

The diagnostic image data is received at a trained classifying device. The term classifying device may particularly refer to a classifier or a classifying unit integrated into a respective apparatus for analyzing diagnostic image data. In some embodiments, the term classifying device may also refer to a classifier provided separate to the apparatus. In some embodiments, the classifying device may particularly be implemented as a convolutional neural network (CNN).

The classifying device is a trained classifying device. That is, the classifying device has previously been trained using a training dataset indicative of the correlation between the diagnostic image data and one or more quantitative features, such as vessel length, vessel location, lesion severity or the like. Specifically, the training is performed using a training dataset including diagnostic image data comparable to the one to be classified which is annotated with the respective quantitative features. Hereby, the annotation may have been obtained by manually annotating the diagnostic image data by a clinical expert, or may be an inherently known ground truth in case simulated training datasets are used.

The weights and parameters of the classifying device, in particular the convoluted neural network, are then optimized in the training process such that for an input of a training dataset the resulting neural network output is numerically close to the corresponding annotated feature values. That is, the optimization of the neural network minimizes on all training datasets the difference between the neural network output and the annotated feature values. The comparison of the neural network output and the annotated feature values may hereby be realized by various types of suitable metrics, e.g. by L2 norm or generalized dice loss. In some examples, the optimization may use an Adam optimizer.

During the training of the classifying device, typically known forms of data augmentation, like image scaling, translation or contrast alteration, may be used. An exemplary network structure for such a task may be an encoder-decoder neural network architecture.

The classifying device is used to classify the diagnostic image data in order to extract at least one quantitative feature from the diagnostic image data. That is, based on the training, the classifying device is enabled to derive, for one or more of the acquisition images in the diagnostic image data, a value for at least one quantitative features of the vessel of interest. In some embodiments, a corresponding value for one particular quantitative feature may be derived per acquisition image. Thus, a plurality of values for a particular quantitative feature may be derived for a plurality of acquisition images.

In some embodiments, the quantitative features may hereby particularly correspond to features such as vessel length, vessel location, vessel diameter, lesion severity, myocardial blush values, visibility score values for the lesions and/or the vessels in the individual acquisition images, i.e. to features that may be derived on a per-image basis.

In some embodiments, the quantitative features may alternatively or additionally include values indicative of the fluid dynamics through the vessel of interest, such as fractional flow reserve (FFR) values, instantaneous wave-free ratio (iFR) values or coronary flow reserve (CFR) values. Conventionally, these parameters may be derived from a fluid dynamics model capable of modeling the fluid dynamics through the vessel of interest as described for example in international applications WO 2016/087396, WO 2020/053099A1 and WO 2019/101630A1. In the present embodiments, it may possible to derive values for these parameters directly from the classifying device. That is, by the training using training datasets, the classifying device may be enabled to implicitly learn the fluid properties of the vessel (s) of interest and, thus, the fluid parameters related thereto without having to simulate or model the fluid flow through the vessel(s) of interest. This allows to avoid using a fluid dynamics model, but rather obtain the fluid parameters directly from the trained classifying device.

On the other hand, the quantitative features may also correspond to features related to the diagnostic image data as a whole, such as completeness scores indicating if sufficient angular information for a vessel of interest is available to obtain a reliable analysis, a reference deviation index indicating if the visible vasculature is similar to a patient averaged reference, or an obstruction score that indicates if a future tomographic reconstruction will likely show strong artefacts if the current trajectory is continued or the like. The obstruction score may hereby particularly be used in the case where implants of specific external devices are in the field of view. That is, in case a particular trajectory results in a device obstructing the field of view in future projections of the planned trajectory, it may be beneficial to change the trajectory to avoid such obstruction.

The quantitative feature is then output associated with the one acquisition image. That is, the value for the quantitative feature that has been derived on the basis of the corresponding acquisition image is associated with said acquisition image and then output for further evaluation and/or further processing. This output is particularly performed while the image acquisition by the medical imaging modality is still in progress.

Based on the output, a computation unit or other processing device then evaluates the at least one quantitative feature, respectively its values, in association with the respective acquisition images in order to determine whether the current acquisition settings used render sufficient image quality. In some embodiments, the computation unit may hereby particularly use quantitative features such as visibility scores, completeness scores or the like. If the evaluation shows that the current acquisition settings do not produce sufficient acquisition images, one or more of the adjustable acquisition settings are adjusted. The adjustment may hereby be performed automatically, in particular on the basis of the previous classification.

The term adjustable acquisition settings may hereby particularly refer to the acquisition settings used that are not pre-defined due to the used medical imaging modality. Accordingly, in the present context, it is distinguished between pre-defined acquisition settings which shall not be changed, i.e. remain the same in order to reduce variability and adjustable acquisition settings which may be changed in accordance with the individual requirements of each patient.

By keeping certain acquisition settings constant and pre-defined while adjusting other acquisition settings based on the automatic analysis of the previously acquired diagnostic image data, it is possible to obtain the diagnostic image data in a reliable, efficient and reproducible manner, while at the same time reducing the variability in the different datasets, acquired at different measurement times for different patients.

More particularly, by analyzing, during diagnostic image data acquisition, the already acquired subset of diagnostic image data, it is possible to perform a "live"-adjustment of the acquisition settings which allows to optimize these acquisition settings for each person individually, thereby obtaining the diagnostic image data in the most efficient manner. This reduces the amount of radiation dose and contrast agent dose to be delivered to the patient since sufficient completeness may be achieved faster for some patients than for others.

In some embodiments, the method may be implemented to perform out-of-distribution detection. That is, the method may be implemented to determine whether the diagnostic image data that is input into the computation unit or other processing device is within the distribution that would be expected based on the training of the classifying device. This may allow detecting if diagnostic image data is input into the computation unit or other processing device that cannot be put into relation with the kind of diagnostic data the classifying device has been trained with.

If that is the case, an indication may be output to a user that the diagnostic image data acquired cannot properly evaluated because it is not related to the kind of diagnostic image data that is expected to be evaluated. This indication may be a simple warning that the diagnostic image data cannot be evaluated or can only be evaluated improperly. Alternatively or additionally, the indication may comprise a suggestion to perform a new or additional diagnostic image data acquisition. In some embodiments, the method may, alternatively or additionally, be implemented to perform an evaluation of the diagnostic image data nonetheless, whereby the output of the evaluation may be done with respectively large error bars.

In some embodiments, the adjusting the one or more adjustable image acquisition settings comprises prematurely terminating the acquisition of the diagnostic image data if it is determined that an already acquired portion of the diagnostic image data fulfils at least one pre-defined reliability criteria.

In some embodiments, the adjustment of the adjustable acquisition settings may particularly comprise terminating the acquisition prior to its planned finishing if it is determined that sufficient diagnostic information has been obtained already. That is, the diagnostic image data acquired is distinguished into two or more subsets of diagnostic image data, whereby the first subset is evaluated while the second subset is currently acquired. The size of each subset may largely depend on the given medical imaging modality and the acquisition quality. A single acquisition image may form a subset. In other embodiments, more acquisition images may form a subset of the diagnostic image data.

The first subset is evaluated such as to determine whether the diagnostic information derived therefrom meets a pre-defined reliability criteria, i.e. whether enough angular information is present to already provide a reliable assessment of the vessel of interest. In some embodiments, the reliability criteria may particularly be quantified in terms of a completeness score. That is, a threshold may be determined for the completeness score and as soon as the completeness score is higher than the threshold, it is determined that sufficient angular information is available for a reliable diagnosis. Alternatively or additionally, the reliability criteria may include further scores and/or criteria.

If it is determined that sufficient information is available, the acquisition setting to be adjusted may in particular be the acquisition ending time. Even more particularly, the acquisition ending time may be set, for example by means of a termination signal, such that the acquisition is immediately terminated. By terminating the acquisition as soon as sufficient information is available, it is possible to keep the radiation dose the patient is subjected to as low as possible. On the other hand, if it is determined that the reliability criteria is not met, i.e. that no sufficient information is available yet, the measurement may continue, i.e. no adjustment of the adjustable acquisition settings is performed. This feedback loop allowing for an adjustment of the acquisition time may be repeated frequently until the acquisition is stopped due to sufficient information being available.

In some embodiments, the adjusting the one or more adjustable acquisition settings comprises adjusting an image acquisition trajectory to improve visibility of the vessel of interest in the diagnostic image data. In some modifications, the adjusting the one or more adjustable acquisition settings comprises adjusting a contrast agent injection rate into the vessel of interest during image acquisition.

In some embodiments, the adjustment of the adjustable image acquisition settings may, additionally or alternatively, comprise an adjusting of the imaging trajectory used for image acquisition. In this case, a visibility score for a vessel of interest and/or a lesion therein is determined for the first subset of diagnostic image data. For that purpose, the entirety of the diagnostic image data is considered and not only the individual acquisition images. The visibility score may be compared to a pre-set reference value or threshold value, whereby the visibility is considered sufficient in case the score is above said value (or below said value) and the visibility is considered poor in case the score is below said value (or above said value): If the visibility score shows that the visibility is not sufficient, i.e. that poor visibility is given, the adjustment of the adjustable imaging settings may particularly comprise an adjustment of the image acquisition trajectory used to acquire the acquisition images. This allows to improve image quality which means that fewer acquisition images are need to obtain sufficient diagnostic information. This effectively reduces the radiation dose delivered to the patient. The adjusted trajectory also avoids that a diagnosis must be made on images with non-ideal visibility.

In some embodiments, the adjusting the one or more adjustable acquisition settings may also encompass the adjusting of a contrast agent injection rate into the vessel of interest. That is, the contrast of the vessel of interest may be determined for the first subset of diagnostic image data using the classifying device. By reviewing the contrast, it may be determined whether sufficient contrast agent has been injected into the vessel of interest. Hereby, the amount of contrast agent may vary from patient to patient since a patient having narrower vessels may need less contrast agent than a patient with wide vessels in order to achieve similar visibility. Thus, based on the contrast of the vessel of interest, it may be evaluated whether there is enough contrast agent in the vessel of interest, and, as such, the contrast injection rate is sufficient or whether it should be adjusted due to too little or too much contrast agent currently being injected into the vessel of interest.

In this case, the adjusting of the adjustable acquisition setting thus comprises adjusting the contrast agent injection rate based on the properties of the vessel of interest. By means of this adjustment the contrast agent dose delivered to each patient may be optimized.

These examples may also be used in a feedback loop whereby the individual subsets of the diagnostic image data may frequently be evaluated during acquisition in order to perform a live-adaptation of the acquisition settings.

In some embodiments, the method further comprises obtaining training image data of the vessel of interest according to the pre-defined acquisition method and extracting the at least one quantitative feature from the training image data, generating at least one training dataset for the classifying device, the training dataset comprising the training image data associated with the at least one quantitative feature, and training the classifying device using the at least one training dataset.

The classifying device may be trained using respective training datasets. In some embodiments, these training datasets may be derived on the basis of training image data. The term training image data may hereby particularly refer to a plurality of training images data having been acquired in a clinical environment, i.e. to measurement data, or to a plurality of training images having been generated by simulation.

Subsequently, one or more quantitative features may be extracted from the individual training images as well as the training image data as a whole. Whether or not individual images or the data as a whole is used hereby depends on the respective quantitative value. The feature extraction may hereby be performed manually by one or more users, automatically by a respective algorithm or may correspond to the quantitative features being readily available from the simulation of the data.

Using the extracted quantitative features and the training image data, a respective training dataset is then generated. That is, the quantitative feature values are associated with the respective training images and/or the training image data in order to derive the correlation between the quantitative feature values and the respective image data. The thus generated training dataset may then be used to train the classifying device.

In yet further embodiments, the training image data comprises simulated training image data generated by simulating an image acquisition according to the pre-defined acquisition method, wherein the simulating comprises the steps of obtaining at least one three-dimensional geometric model of the vessel of interest, obtaining at least one two-dimensional background image for the vessel of interest, and simulating a contrast agent fluid dynamic through the patient's vasculature based on at least one contrast agent fluid parameter. In some modifications, the simulating further comprises obtaining deformation translation and rotation data, and augmenting the simulated training image data based on the translation and rotation data. In some modifications, the generating the at least one training dataset further comprises the steps of receiving additional patient data, and adjusting the at least one training dataset in accordance with the additional patient data.

In some embodiments, the training image data is generated by means of a simulation. For that purpose, at least one three-dimensional geometric model of a patient's vasculature including the vessel of interest is obtained. Hereby, the geometric model may be obtained from a medical image which may have been acquired by any medical imaging modality that allows to acquire three-dimensional medical images.

In some embodiments, the medical imaging modality may correspond to the medical imaging modality for which the live adaptation shall be performed. In some embodiments, the medical imaging modality may be a different imaging modality. The geometrical model may also be purely virtual, and defined by common anatomical knowledge. Further, at least one two-dimensional background image of the vasculature of the patient including the vessel of interest is acquired. By means of the background image, it is possible to distinguish the background and the vasculature in the medical images in order to properly perform a vessel identification of the vessels in the vasculature.

The background image may also provide a realistic appearance to the simulated data. The two-dimensional background image may hereby have been obtained from an actual clinical acquisition and/or it may have been constructed from a forward projection of a three-dimensional medical image and/or it may be a virtual image designed to mimic typical background seen in the diagnostic data that is to be simulated.

Additionally, the three-dimensional medical image and/or the two-dimensional background image may be used to generate a fluid dynamics model representative of the fluid dynamics through the patient's vasculature. In some embodiments the fluid dynamics model may particularly comprise a lumped parameter model.

The term lumped parameter model may particularly refer to a model in which the fluid dynamics of the vessels are approximated by a topology of discrete entities. As an example, a vasculature, such as a vessel tree, may be represented by a topology of resistor elements each having a particular resistance. Accordingly, the outlet at a distal end of the vessel is also represented by a particular resistor element. This resistor element is then connected to ground such as to represent the termination of the vessel. Similarly, respective resistor elements may be connected to the series of resistor elements representing the vessel of interest, such as to represent the outflow from the vessel of interest at certain bifurcations. These resistor elements may typically also be connected to ground.

These lumped parameter models reduce the number of dimensions compared to other approaches such as Navier-Stokes or the like. Accordingly, using a lumped parameter model may allow for a simplified calculation of the fluid dynamics inside the vessels and may ultimately result in reduced processing time. The employing of such a lumped parameter model is described for example in international application WO 2016/087396.

The thus generated fluid dynamics model may then be employed to simulate a contrast agent fluid flow through the patient's vasculature and, in particular, through the vessel or vessels of interest. This allows to generate training image data representative of the vasculature and the corresponding fluid dynamics through it. In some embodiments, in order to augment the training image data, deformation translation and rotation data may be added to the simulation as additional information. The thus generated training image data may then be provided to the classifying device for training.

In some embodiments, the at least one quantitative feature comprises one or more of: a vessel label of a vessel in the patient's vasculature and/or a vessel length of a vessel in the patient's vasculature and/or a severity of a lesion in a vessel in the patient's vasculature and/or a vessel diameter of a vessel in the patient's vasculature and/or a visibility score for a lesion and/or a vessel in the patient's vasculature and/or a completeness score for the at least one of the plurality of acquisition images and/or a myocardial blush value.

In some embodiments, additional patient information such as ECG data, aortic pressure value or historical data for a particular patient may also be added to the training datasets and/or the classification. This may have the further benefit that additional patient anomalies such as strongly elevated aortic pressure may be detected as, in those cases, the injection of the contrast agent may have to be adjusted as well.

According to some embodiments, the outputting the at least one quantitative feature for further evaluation comprises the steps of displaying the at least one quantitative feature to a user and/or outputting the at least one quantitative feature in a pre-defined format for automatic reporting to a reporting entity. In some embodiments, the user may input additional data in response to the outputting, whereby the additional data may further be used to train the classifying device and/or to evaluate the diagnostic image data.

According to a further aspect, an apparatus for analyzing diagnostic image data is provided, the apparatus comprising a trained classifying device configured to receive diagnostic image data comprising a plurality of acquisition images of a vessel of interest, the diagnostic image data having been acquired using a pre-defined acquisition method, classify the diagnostic image data to extract at least one quantitative feature of the vessel of interest from at least one acquisition image of the plurality of acquisition images, and output the at least one quantitative feature of the vessel of interest associated with the at least one acquisition image while the acquisition of the diagnostic image data is still in progress, and a computation unit configured to adjust one or more adjustable image acquisition settings based on the at least one quantitative feature to optimize the acquisition of the diagnostic image data.

In some embodiments, the apparatus further comprises an input unit configured to obtain training image data of the vessel of interest according to the pre-defined acquisition method, a training dataset generation unit configured to extract the at least one quantitative feature of the vessel of interest from the training image data and to generate at least one training dataset for the classifying device, the training dataset comprising the training image data associated with the at least one quantitative feature, and to provide the at least one training dataset to the classifying device for training. In some embodiments, the apparatus may also comprise a display unit configured to generate a graphical representation of at least one acquisition image of the plurality of acquisition images and/or the at least one quantitative feature, and a user interface configured to receive user inputs in response to the graphical representation.

In a further aspect, a computer program for controlling an apparatus according to the invention is provided, which, when executed by a processing unit, is adapted to perform the method steps according to the invention. In an even further aspect, a computer-readable medium is provided having stored thereon the above-cited computer program.

It shall be understood that the method of claim 1, the apparatus of claim 11, the computer program of claim 14, and the computer-readable medium of claim 15, have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

The illustration in the drawings is schematically. In different drawings, similar or identical elements are provided with the same reference numerals.

Figure 1:
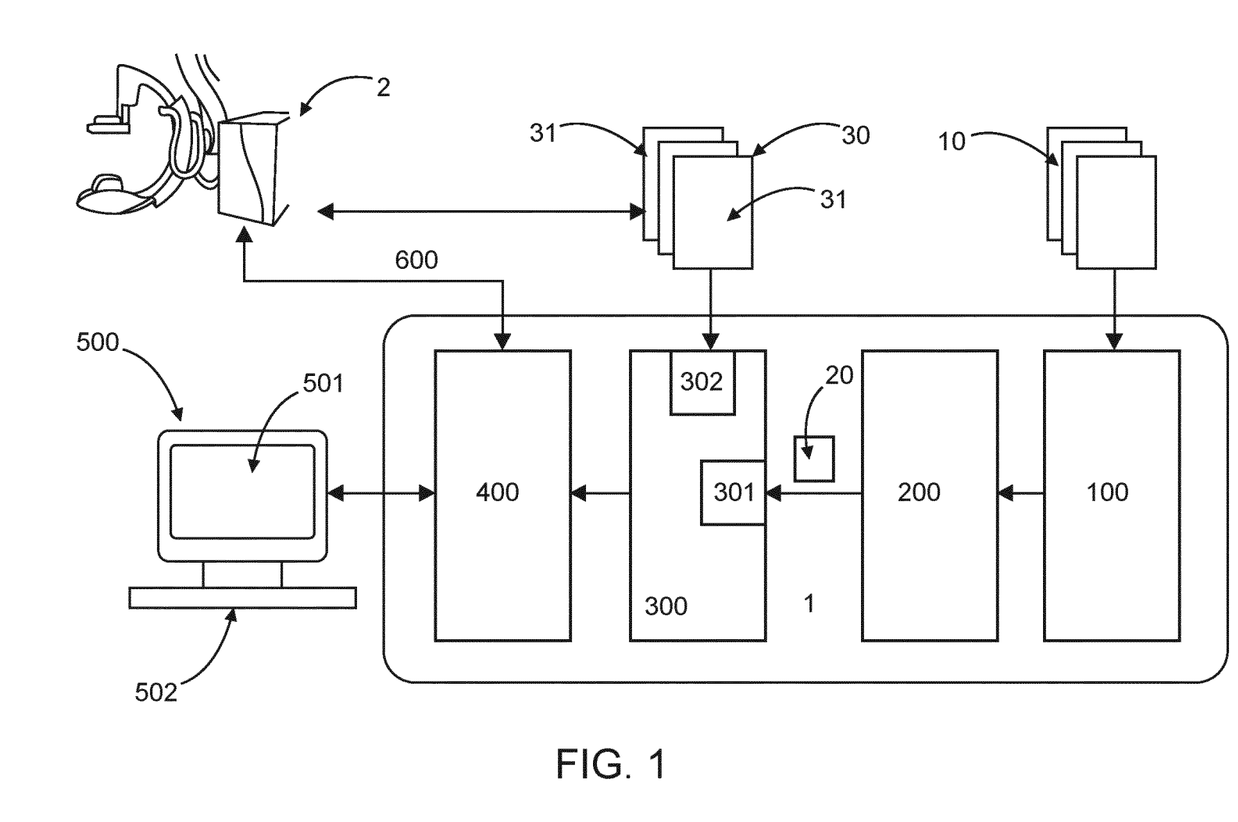
FIG. 1 schematically illustrates an apparatus for analyzing diagnostic image data vessels according to an embodiment.

FIG. 1 represents schematically an exemplary embodiment of an apparatus 1 for analyzing diagnostic image data. The apparatus 1 comprises an input unit 100, a training dataset generation unit 200, a classifying unit 300, a computation unit 400 and a display unit 500. Further, the classifying unit 300 and the communication unit 400 are communicatively coupled to a medical imaging modality 2 in a feedback loop 600.

Input unit 100 is configured to receive training image data 10 of a patient's vasculature. The training image data 10 may particularly correspond to or comprise image data that has been previously acquired using a pre-defined acquisition method, i.e. an acquisition method performed with one or more pre-defined (known) acquisition settings, such as known contrast agent dose and acquisition trajectory. In the specific embodiment according to FIG. 1, the training image data 10 may particularly correspond to clinical data that has been acquired by means of X-ray angiography using a C-arm. That is, in the specific embodiment of FIG. 1, the training image data 10 has been derived from actual measurement data.

It shall be understood, though, that alternatively or additionally, the training image data 10 may also have been generated using a simulation or the like. For simulated training image data 10, three-dimensional medical images, usually acquired using the CT and/or MR imaging modality, may be acquired, used to generate a three-dimensional model of the vessel of interest and combined with two-dimensional background data showing cardiac images without any contrast agent filling of the arteries. Based on the contrast injection parameters used for the pre-defined acquisition method and a corresponding fluid dynamics model, training image data and a corresponding training dataset is generated. Hereby, deformations translations and rotations may be added to the three-dimensional representation of the vessel of interest and the two-dimensional background projection to achieve data augmentation. The full range of the acquisition trajectory is then typically covered by a cardiac motion model.

Input unit 100 provides the training image data 10 to training dataset generation unit 200. Training dataset generation unit 200 is configured to extract one or more quantitative features of the patient's vasculature, and, in particular, the vessel of interest, from the training image data 10. In some embodiments, these quantitative features may particularly relate to vessel labels, vessel numbers, vessel location and/or the vessel length of the vessels in the vasculature, the severity of a lesion or multiple lesions in one or more vessels of interest, a myocardial blush value, a vessel diameter of the vessel of interest, a visibility score for a lesion in the vessel of interest for each individual training image of the training image data, a completeness score indicating if sufficient angular information for a given vessel is available to allow for a reliable analysis, a reference deviation index, indicating of the visible vasculature is similar to a reference, or the like.

Using the extracted quantitative features, the training dataset generation unit 200 is configured to generate at least one training dataset comprising the training image data 10 and the respective pre-defined features that are associated with one or more of the training images in the training image data 10. The training dataset generation unit 200 thus obtains a correlation between the training image data 10 and the extracted pre-defined features and generates a corresponding dataset comprising the correlated information. This corresponding dataset is then provided, as a training dataset 20, to the classifying unit—or classifying device—300.

Classifying unit 300 comprises an input port 301 configured to receive the training dataset from training dataset generation unit 200. Classifying device 300 uses the training dataset 20—or, optionally, multiple training datasets 20—to train the relation between the quantitative features and the training images in the training image data 10. In the exemplary embodiment according to FIG. 1, classifying unit comprises or corresponds to a convolutional neural network, in some embodiments a deep convolutional neural network. That is, classifying unit 400 implements a plurality of convolutional layers in combination with a pooling layer.

The training dataset 20 input into classifying unit 300 according to the specific embodiment of FIG. 1 corresponds to a plurality of training images having been acquired using X-ray angiography. In particular, in the specific embodiment of FIG. 1 10.000 individual angiography images are used as respective training images. These training images are provided with respective feature data in terms of a pixel mask that is provided for each individual angiography image, whereby each pixel is either classified as belonging to the left anterior descending artery (LAD), the left circumflex artery (LCX), the obtuse marginal branches (OM), the right coronary artery or the like arteries, or as belonging to the background. Alternatively or additionally, the training images may be provided with feature data comprising, for each angiography image, a single value indicating the minimal diameter of the arteries, and/or indicating that (parts of) the arteries are not visible.

During training, the weights and parameters of the classifying device 300, in the specific embodiment according to FIG. 1 the neural network, are optimized so that for the input training dataset 20, the resulting neural network output is numerically close to the corresponding annotated feature values. That is, the optimization of the neural network minimizes on all training datasets the difference between the neural network output and the annotated feature values. Hereby, the comparison of the neural network output and the annotated feature values can be realized by various types of suitable metrics, such as for example L2 norm or generalized dice loss. In the specific embodiment according to FIG. 1, the optimization may particularly use an Adam optimizer.

During training, typical known forms of data augmentation like image scaling, translation or contrast alteration may be used. An exemplary network structure for such a task may be an encoder-decoder neural network architecture.

Upon finalizing training using the training dataset 20, the classifying unit 300 is configured to receive, via input port 302, from the medical imaging modality 2, a first subset of diagnostic image data 30 obtained for a particular patient. The first subset of diagnostic image data 30 may particularly comprise a plurality of acquisition images 31 that have been acquired using a pre-defined acquisition method, whereby the pre-defined acquisition method corresponds to the pre-defined acquisition method for the training image data in order to ensure that the classifying unit 300 has been trained with the proper training datasets to accurately classify the diagnostic image data 30.

In the specific embodiment of FIG. 1, the input to the classifying device corresponds to the plurality of acquisition images 31 in the diagnostic image data 30, each acquisition image 31 corresponding to a single two-dimensional X-ray angiography image. Alternatively, the plurality of acquisition mages 31 may also correspond to a chronological stack of multiple two-dimensional angiography images, such as respective C-arm angulations. That is, the input to the classifying device corresponds to the same diagnostic image data 30 that is presented to the user, such as the physician, for visual review.

Upon classification of the diagnostic image data, at least one quantitative feature that is suitable for analyzing the diagnostic image data 30 is extracted from the diagnostic image data 30.

The extracted quantitative feature values and the first subset of diagnostic image data 30 comprising the one or more acquisition images 31 are then provided to computation unit 400 for further processing. It shall be understood that the first subset of diagnostic image data 30 is provided to the computation unit 400 for further processing while the acquisition of the second subset of diagnostic image data 30 is still in progress. This allows to use the evaluation by computation unit 400 to adjust the image acquisition where possible and/or necessary.

In other words, the computation unit 400 determines, based on the first subset of diagnostic image data and the extracted quantitative features, whether an adjustment of the acquisition parameters for the image acquisition may be beneficial. In the specific example of FIG. 1, computation unit 400 derives, for that purpose, a reliability criteria for the diagnostic information to be derived from the diagnostic image data 30 and the quantitative features.

Further, the computation unit 400 processes the first subset of diagnostic image data 30 and the quantitative features derived therefrom and determines whether the reliability criteria is met or not. In the specific embodiment, this is achieved by comparing the diagnostic information that may be derived from the first subset of diagnostic image data 30 and the quantitative features to a threshold value which indicates sufficiency of the diagnostic information.

It is considered that the reliability criteria is met if sufficient diagnostic information may be derived. In this case, the computation unit 400 is then configured to adjust the adjustable image acquisition settings by outputting a corresponding termination signal to medical imaging modality 2, i.e. by adjusting the acquisition settings such that the acquisition is prematurely terminated, i.e. finished prior to its originally set termination point. That is, in response to said termination signal, medical imaging modality 2 terminates the further image acquisition, thereby avoiding unnecessary radiation and contrast agent dose to be delivered to the patient.

On the other hand, if the computation unit 400 determines that the reliability criteria is not met, i.e. that no sufficient information is available yet, the computation unit 400 will not output any termination signal to the medical imaging modality 2 and the medical imaging modality 2 will continue acquisition of a second subset of diagnostic image data.

It shall be understood that the above-described evaluation process may be repeated for the second subset of diagnostic image data 30 (and any subsequent subset) until the reliability criteria are met. The computation unit 400 may hereby terminate the acquisition procedure as soon as it is determined that sufficient diagnostic information is available.

In some embodiments, the adjustment of the adjustable image acquisition settings may, additionally or alternatively, comprise an adjusting of the imaging trajectory used for image acquisition. In this case, evaluating the first subset of diagnostic image data 30 may comprise determining a visibility score for a vessel of interest in the individual acquisition images. If the computation unit 400 registers poor visibility, the computation unit 400 may be configured to automatically adjust the imaging trajectory to improve visibility of the vessel of interest. By adjusting the imaging trajectory in order to improve visibility, less acquisition images 31 are required to obtain sufficient diagnostic information, thereby optimizing the radiation dose delivered to the patient.

In other embodiments, the computation unit 400 may also evaluate the first subset of diagnostic image data 30 along with the extracted quantitative features in order to determine a contrast of the vessel of interest. This allows to determine whether sufficient contrast agent has been injected into the vessel of interest. The amount of contrast agent necessary to provide sufficient visibility of the vessel(s) of interest may vary from patient to patient. Hereby, a patient having narrower vessels may need less contrast agent, whereby a patient with wide vessels may need more contrast agent in order to achieve similar visibility. Accordingly, the computation unit 400 may be configured to adjust, as a further adjustable acquisition setting, the contrast agent injection rate based on the properties of the vessel of interest, whereby a lower rate is used for patients having narrow vessels (i.e. requiring less contrast agent) and a higher rate is used for patients having wider vessels (i.e. requiring more contrast agent). By means of this adjustment, the contrast agent dose delivered to each patient may be optimized.

It shall be understood that, for these examples as well, the above-described evaluation process may be repeated for a second subset of diagnostic image data 30 (and any subsequent subset) until the reliability criteria are met, i.e. until sufficient diagnostic information is available.

It shall further be understood that the different adjustment procedures may also be combined with one another. As such, the computation unit 400 may be configured to adjust the contrast agent injection rate in accordance with the respective vessel properties for the patient and to further terminate the acquisition procedure as soon as it is determined that sufficient diagnostic information is available.

By means of this arrangement, a feedback loop is implemented which allows a live adaptation of the acquisition parameters in order to optimize diagnostic image data acquisition.

In the exemplary embodiment of FIG. 1, the diagnostic image data 30, along with the extracted features, is further provided to a display unit 500. The display unit 500 may particularly comprise a screen 501 for displaying information graphically and a user interface 502, such as a keyboard, a touchpad, a mouse, a touchscreen or the like configured to allow the user to provide inputs and generally operate the device.

The display unit 500 is configured to generate a graphical representation of the image data 30 and the extracted quantitative features and to present this information to a user on screen 501. The user may then review the presented information and provide respective input thereon via the user interface 502. The user input may then be used for further evaluation of the data. In some embodiments, the user input may also be used to be returned to the trained classifying unit 300 and used, by the classifying unit, for further training.

Figure 2:
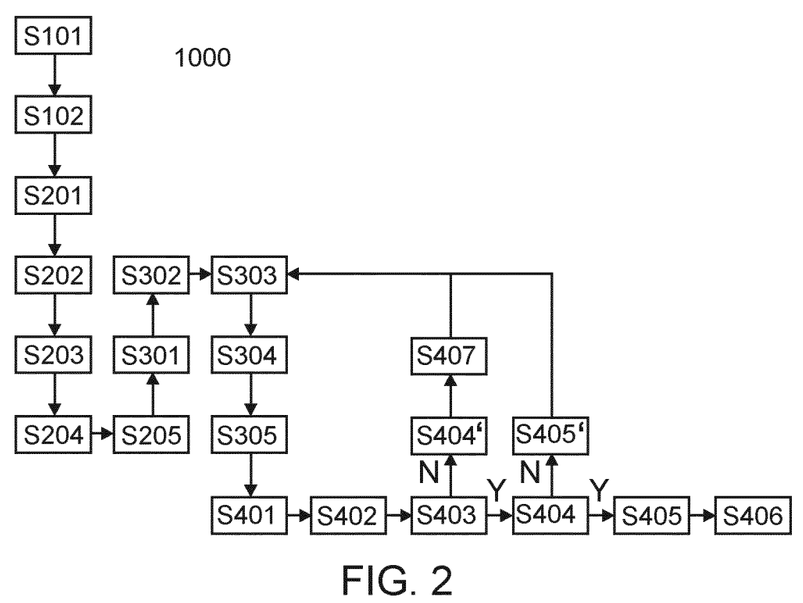
FIG. 2 shows a flow chart of a method for analyzing diagnostic image data according to an embodiment.

FIG. 2 shows a flow chart of a method 1000 for analyzing diagnostic image data using an apparatus 1 in accordance with FIG. 1. At step S101 the input unit 100 to receives training image data 10 that may have been generated as explained in relation to FIG. 3. Alternatively or additionally, the training image data may also have been generated by different means.

At step S102, the input unit 100 provides the training image data 10 to training dataset generation unit 200. At step S201, the training dataset generation unit 200 receives the training image data 10 and, in step S202, extracts one or more quantitative features of the patient's vasculature, in particular of one or more vessels of interest in the patient's vasculature, from the training image data 10. Optionally, the training dataset generation unit 200 correlates the one or more quantitative features to the training image data 10 in step S203.

In step S204, the training dataset generation unit 200 generates at least one training dataset. This at least one training dataset 20 is provided to the classifying unit 300 in step S205.

In step S301, classifying unit 300 receives the training dataset 20 from training dataset generation unit 200. In step S302, classifying unit 300 then uses the training dataset 20 for training as described in relation to FIG. 1.

Subsequently, the classifying unit 300, in step S303, receives a first subset of diagnostic image data 30 acquired by medical imaging modality 2. In step S304, the classifying unit 300 classifies the plurality of acquisition images in the first subset of diagnostic image data 30 to extract at least one quantitative feature, in particular at least one value for the at least one quantitative feature, from at least one acquisition image 31 of the diagnostic image data 30.

The classification is hereby performed based on the previous training using the training dataset 20. In step S305, classifying unit 300 provides the diagnostic image data 30 along with the extracted features to computation unit 400 for further processing. It shall hereby again be understood that the first subset of diagnostic image data 30 is provided to the computation unit 400 for further processing while the acquisition of a second subset of diagnostic image data 30 is still ongoing, thereby allowing to use the evaluation by computation unit 400 to adjust the image acquisition.

For that purpose, computation unit 400 receives, in step S401, the first subset of diagnostic image data 30 along with the extracted quantitative feature, and evaluates, in step S402, the received data in order to determine whether adjustment of one or more adjustable acquisition settings may be necessary. In the specific embodiment of FIG. 2, this means that the computation unit 400 determines, based on the first subset of diagnostic image data 30, a visibility score for a vessel of interest in each of the individual acquisition images 31 in the diagnostic image 30. In step S403, the computation unit 400 then compares the visibility score to a reference value in order to determine whether the visibility of the vessel of interest is sufficient or whether it needs to be improved.

In the former case ("Y"), i.e. in the case where the visibility is sufficient, the method proceeds to step S404. If, in step S403, the latter is the case ("N"), i.e. the visibility needs to be improved, the method proceeds to step S404'. In step S404', the computation unit 400 determines an optimized imaging trajectory in order to improve visibility and, in step S407 generates a corresponding adjustment signal and provides said adjustment signal to medical imaging modality 2 to automatically adjust the imaging trajectory. In response to the adjustment signal, the medical imaging modality adjusts the imaging trajectory used to acquire the second subset of diagnostic image data 30. The method is then repeated in a loop starting from step S303 with the second subset of diagnostic image data 30.

As indicated herein above, if is determined in step S403, that the visibility is sufficient ("Y"), the method proceeds to step S404. In step S404, the computation unit 400 evaluates the first subset of diagnostic image data 30 in order to determine whether sufficient diagnostic information may be derived from the accumulation of acquisition images 31 in the first subset of diagnostic image data 30. If that is the case ("Y"), computation unit 400 generates a termination signal and provides said termination signal to the medical imaging modality 2 in step S545. This results in the termination of the image acquisition in step S406.

If this is not the case ("N"), i.e. if it is determined in step S404 that the diagnostic information that may be derived from the accumulation of acquisition images 31 in the first subset of diagnostic image data 30 is not sufficient, the method proceeds to step S405'. In step S405' no termination signal is generated and the method proceeds to continue with the second subset (or a subsequent subset) of diagnostic image data 30 being received and processed in steps S303 to S404. By means of this arrangement, a feedback loop is implemented which allows a live adaptation of the acquisition parameters in order to optimize diagnostic image data acquisition.

Figure 3:
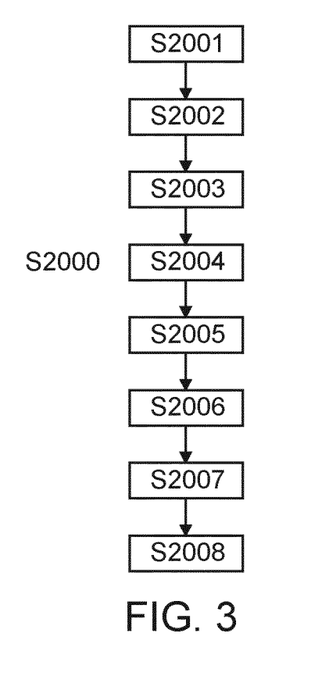
FIG. 3 shows a flow chart of a method for generating the training data according to an embodiment.

FIG. 3 shows a flow chart of a method 2000 for generating training image data according to an embodiment. In step S2001, a simulation unit obtains at least one medical image of the patient and generates a three-dimensional geometric model of said patient's vasculature therefrom. The medical image may particularly have been obtained by a medical imaging modality. The medical imaging modality may correspond to medical imaging modality 2 or may be a different imaging modality.

In step S2002, the simulation unit further obtains at least one two-dimensional background image of the vasculature of the patient in order to accurately distinguish background from vasculature.

In step S2003, the simulation unit then performs a vessel identification and identifies the vessels in the vasculature. Further, in step S2004, the simulation unit uses the three-dimensional medical image and/or the two-dimensional background image to generate a fluid dynamics model of the blood flow through the patient's vasculature. In the specific embodiment according to FIG. 3, the fluid dynamics model may comprise or correspond to a lumped parameter model, i.e. a model in which the fluid dynamics of the vessels are approximated by a topology of discrete entities.

This model is used, in step S2005 to simulate a contrast agent fluid flow through the patient's vasculature. In step S2006, the simulation unit may optionally further receive deformation translation and rotation data as additional information. In step S2007, the simulation unit may then use the additional information in order to augment the training image data. In step S2008, the training image data is output to be provided to the classifying unit 400.

Although in the above-cited embodiments, the training data has been generated based on a simulation using a fluid dynamics model, it shall be understood that the training data may also be derived from historical clinical data of one or more patients.

Although in the above embodiments, the adjustment of the adjustable acquisition parameter concerned a change in imaging trajectory and a termination of the acquisition process, it shall be understood that other kinds of adjustments may be made automatically on the basis of the classification of the already received diagnostic image data, such as an adjustment of the radiation dose to be delivered to a target region and/or an adjustment of the injection rate into the vessel of interest and so on.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the generating of the training dataset, the training of the classifying device, the classifying of the image data, the simulation of the training image data to generate the training image data or the like that may have been explained to be performed by a single unit may also be performed by multiple units. Also, certain procedures may be performed by the same unit, rather than separate units.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a method for analyzing diagnostic image data, comprising the steps of receiving diagnostic image data comprising a plurality of acquisition images of a vessel of interest at a trained classifying device, the diagnostic image data having been acquired using a pre-defined acquisition method, classifying the diagnostic image data to extract at least one quantitative feature of the vessel of interest from at least one acquisition image of the plurality of acquisition images, outputting the at least one quantitative feature of the vessel of interest associated with the at least one acquisition image while the acquisition of the diagnostic image data is still in progress, and adjusting one or more adjustable image acquisition settings based on the at least one quantitative feature to optimize the acquisition of the diagnostic image data.

The invention claimed is:
1. A computer-implemented method for analyzing diagnostic image data, the method comprising:
receiving diagnostic image data comprising a plurality of acquisition images of a vessel of interest at a trained classifying device, wherein the diagnostic image data is acquired using a pre-defined acquisition method, classifying the diagnostic image data to extract at least one quantitative feature of the vessel of interest from at least one acquisition image of the plurality of acquisition images, outputting the at least one quantitative feature of the vessel of interest associated with the at least one acquisition image while the acquisition of the diagnostic image data is still in progress, and adjusting one or more adjustable image acquisition settings based on the at least one quantitative feature to optimize the acquisition of the diagnostic image data.

2. The method according to claim 1, wherein the adjusting the one or more adjustable image acquisition settings comprises:

prematurely terminating the acquisition of the diagnostic image data if it is determined that an already acquired portion of the diagnostic image data fulfils at least one pre-defined reliability criteria.

3. The method according to claim 1, wherein the adjusting the one or more adjustable acquisition settings comprises:

adjusting an image acquisition trajectory to improve visibility of the vessel of interest in the diagnostic image data.

4. The method according to claim 1, wherein the adjusting the one or more adjustable acquisition settings comprises:

a contrast agent injection rate into the vessel of interest during image acquisition.

5. The method according to claim 1, further comprising:

obtaining training image data of the vessel of interest according to the pre-defined acquisition method and extracting the at least one quantitative feature from the training image data, generating at least one training dataset, the training dataset comprising the training image data associated with the at least one quantitative feature, and training the classifying device using the at least one training dataset.

6. The method according to claim 5, wherein the training image data comprises simulated training image data generated by simulating an image acquisition according to the pre-defined acquisition method, wherein the simulating comprises:

obtaining at least one three-dimensional geometric model of the vessel of interest;

obtaining at least one two-dimensional background image for the vessel of interest; and simulating a contrast agent fluid dynamic through the patient's vasculature based on at least one contrast agent fluid parameter.

7. The method according to claim 6, wherein the simulating further comprises:

obtaining deformation translation and rotation data, and augmenting the simulated training image data based on the translation and rotation data.

8. The method according to claim 5, wherein the generating the at least one training dataset further comprises:

receiving additional patient data, and adjusting the at least one training dataset in accordance with the additional patient data.

9. The method according to claim 1, wherein the at least one quantitative feature comprises one or more of: a vessel label of a vessel in the patient's vasculature, or a vessel length of a vessel in the patient's vasculature, a severity of a lesion in a vessel in the patient's vasculature, a vessel diameter of a vessel in the patient's vasculature, a visibility score for a lesion, a vessel in the patient's vasculature, a completeness score for the at least one of the plurality of acquisition images, and a myocardial blush value.

10. The method according to claim 1 wherein the outputting the at least one quantitative feature for further evaluation comprises at least one of:

displaying the at least one quantitative feature to a user, and outputting the at least one quantitative feature in a pre-defined format for automatic reporting to a reporting entity.

11. An apparatus for analyzing diagnostic image data, the apparatus comprising:

a processor in communication with memory, the processor configured to:

receive diagnostic image data comprising a plurality of acquisition images of a vessel of interest, wherein the diagnostic image data is acquired using a pre-defined acquisition method, classify the diagnostic image data to extract at least one quantitative feature of the vessel of interest from at least one acquisition image of the plurality of acquisition images, and output the at least one quantitative feature of the vessel of interest associated with the at least one acquisition image while the acquisition of the diagnostic image data is still in progress, and adjust one or more adjustable image acquisition settings based on the at least one quantitative feature to optimize the acquisition of the diagnostic image data.

12. The apparatus according to claim 11, further comprising:

a second processor in communication with memory, the second processor configured to:

obtain training image data of the vessel of interest according to the pre-defined acquisition method, extract the at least one quantitative feature of the vessel of interest from the training image data, generate at least one training dataset comprising the training image data associated with the at least one quantitative feature, and provide the at least one training dataset to the processor for training.

13. The apparatus according to claim 11, wherein the processor is further configured to:

generate a graphical representation of one or more of: at least one acquisition image of the plurality of acquisition images and the at least one quantitative feature, and receive user inputs in response to the graphical representation.

14. A non-transitory computer-readable medium having stored a computer program comprising instructions which, when executed by a processor, cause the processor to:

receive diagnostic image data comprising a plurality of acquisition images of a vessel of interest at a trained classifying device, wherein the diagnostic image data is acquired using a pre-defined acquisition method, classify the diagnostic image data to extract at least one quantitative feature of the vessel of interest from at least one acquisition image of the plurality of acquisition images, output the at least one quantitative feature of the vessel of interest associated with the at least one acquisition image while the acquisition of the diagnostic image data is still in progress, and adjust one or more adjustable image acquisition settings based on the at least one quantitative feature to optimize the acquisition of the diagnostic image data.

15. The non-transitory computer-readable medium according to claim 14, wherein the instructions, when executed by the processor, further cause the processor to:
   obtain training image data of the vessel of interest according to the pre-defined acquisition method and extracting the at least one quantitative feature from the training image data,
   generate at least one training dataset for the classifying device, the training dataset comprising the training image data associated with the at least one quantitative feature, and
   train the classifying device using the at least one training dataset.

16. The non-transitory computer-readable medium according to claim 15, wherein the training image data comprises simulated training image data generated by simulating an image acquisition according to the pre-defined acquisition method, and,
   to simulate the image acquisition, the instructions, when executed by the processor, further cause the processor to:
   obtain at least one three-dimensional geometric model of the vessel of interest;
   obtain at least one two-dimensional background image for the vessel of interest; and
   simulate a contrast agent fluid dynamic through the patient's vasculature based on at least one contrast agent fluid parameter.

17. The non-transitory computer-readable medium according to claim 16, wherein, to simulate the image acquisition, the instructions, when executed by the processor, further cause the processor to:
   obtain deformation translation and rotation data, and
   augment the simulated training image data based on the translation and rotation data.

18. The apparatus according to claim 11, wherein the processor is further configured to:
   obtain training image data of the vessel of interest according to the pre-defined acquisition method and extracting the at least one quantitative feature from the training image data,
   generate at least one training dataset for the classifying device, the training dataset comprising the training image data associated with the at least one quantitative feature, and
   train the classifying device using the at least one training dataset.

19. The apparatus according to claim 18, wherein the training image data comprises simulated training image data generated by simulating an image acquisition according to the pre-defined acquisition method, and,
   to simulate the image acquisition, the processor is further configured to:
   obtain at least one three-dimensional geometric model of the vessel of interest;
   obtain at least one two-dimensional background image for the vessel of interest; and
   simulate a contrast agent fluid dynamic through the patient's vasculature based on at least one contrast agent fluid parameter.

20. The apparatus according to claim 19, wherein, to simulate the image acquisition, the processor is further configured to:
   obtain deformation translation and rotation data, and
   augment the simulated training image data based on the translation and rotation data.

* * * * *